United States Patent
Rosenwald et al.

(10) Patent No.: US 11,376,263 B2
(45) Date of Patent: Jul. 5, 2022

(54) CYPROTERONE ACETATE COMPOSITIONS AND USES THEREOF

(71) Applicant: FORTRESS BIOTECH, INC., New York, NY (US)

(72) Inventors: Lindsay Rosenwald, New York, NY (US); Lei Zheng, New York, NY (US); Lucy Lu, New York, NY (US)

(73) Assignee: Fortress Biotech, Inc., New York, NY (US)

( * ) Notice: Subject to any disclaimer, the term of this patent is extended or adjusted under 35 U.S.C. 154(b) by 0 days.

(21) Appl. No.: 17/329,762

(22) Filed: May 25, 2021

(65) Prior Publication Data

US 2022/0110947 A1 Apr. 14, 2022

Related U.S. Application Data

(60) Provisional application No. 63/089,410, filed on Oct. 8, 2020.

(51) Int. Cl.
| | | |
|---|---|---|
| *A61K 31/573* | (2006.01) | |
| *A61K 9/00* | (2006.01) | |
| *A61P 15/08* | (2006.01) | |
| *A61P 15/18* | (2006.01) | |
| *A61K 31/567* | (2006.01) | |

(52) U.S. Cl.
CPC .......... *A61K 31/573* (2013.01); *A61K 9/0053* (2013.01); *A61K 31/567* (2013.01); *A61P 15/08* (2018.01); *A61P 15/18* (2018.01)

(58) Field of Classification Search
CPC .. A61K 31/573; A61K 31/567; A61K 9/0053; A61P 15/08; A61P 15/18
See application file for complete search history.

(56) References Cited

U.S. PATENT DOCUMENTS

| | | |
|---|---|---|
| 3,957,982 A | 5/1976 | Lachnit-Fixson et al. |
| 3,969,502 A | 7/1976 | Lachnit-Fixson |
| 4,344,942 A | 8/1982 | Blandamura |
| 4,639,440 A | 1/1987 | Blandamura |
| 5,756,490 A | 5/1998 | Lachnit |
| 6,312,722 B1 | 11/2001 | Schmidt-Gollwitzer et al. |
| RE37,564 E | 2/2002 | Spona et al. |
| RE37,838 E | 9/2002 | Spona et al. |
| RE38,253 E | 9/2003 | Spona et al. |
| RE43,916 E | 1/2013 | Spona et al. |

(Continued)

FOREIGN PATENT DOCUMENTS

WO  WO 1995/017194  6/1995

OTHER PUBLICATIONS

Diane-35, product package insert, 1988. (Year: 1998).*

(Continued)

*Primary Examiner* — San Ming R Hui
(74) *Attorney, Agent, or Firm* — DLA Piper LLP (US)

(57) ABSTRACT

Provided herein are oral drug preparations including cyproterone acetate and ethinylestradiol, dosing regimen for the drug preparations, and methods of treating diseases. The methods provided include the administration of the oral drug preparation to treat one or more symptoms of hyperandrogenic conditions or hyperandrogenic activities, to provide contraception, and to reduce a risk of vascular thromboembolism (VTE) in a subject.

30 Claims, 2 Drawing Sheets

(56) References Cited

U.S. PATENT DOCUMENTS

RE44,159 E     4/2013    Spona et al.

OTHER PUBLICATIONS

Edelman et al., Cochrane Database Syst Rev, Jul. 29, 2014;2014(7):CD004695 (Year: 2014).*

Christin-Maitre et al., "Comparison of a 24-day and a 21-day pill regimen for the novel combined oral contraceptive, nomegestrol acetate and 17β-estradiol (NOMAC/E2): a double-blind, randomized study", Human Reproduction, Mar. 2011, 26(6):1338-1347.

Jones et al., "Hair growth and androgen responses in hirsute women treated with continuous cyproterone acetate and cyclical ethinyl oestradiol" European Journal of Endocrinology, Dec. 1987, 116(4):497-501.

Karakurt et al., "Comparison of the Clinical Efficacy of Flutamide and Spironolactone plus Ethinyloestradiol/Cyproterone Acetate in the Treatment of Hirsutism: a Randomised Controlled Study", Adv Ther, 2008, 25(4):321-328.

Nguyen et al., "Cyproterone acetate in the treatment of oestrogen hypersensitivity vulvovaginitis". Australasian Journal of Dermatology, 2018, 59:52-54.

Porcile et al., "Long-term treatment of hirsutism: desogestrel compared with cyproterone acetate in oral contraceptives", Fertil Steril., May 1991, 55(5):877-881.

Wang et al., "Comparison of Drospirenone—with Cyproterone Acetate—Containing Oral Contraceptives, Combined with Metformin and Lifestyle Modification in Women with Polycystic Ovary Syndrome and Metabolic Disorders: A Prospective Randomized Control Trial", Chinese Medical Journal, Apr. 2016, 129(8):883-890.

PCT ISR and Written Opinion in International Application No. PCT/US2021/054038, dated Feb. 2, 2022, 7 pages.

\* cited by examiner

CYPROTERONE ACETATE COMPOSITIONS AND USES THEREOF

CROSS-REFERENCE TO RELATED APPLICATIONS

This application claims the benefit of priority under 35 U.S.C. § 119(e) of U.S. Provisional Application No. 63/089,410, filed Oct. 8, 2020. The contents of the forementioned application are herein incorporated by reference in its entirety.

BACKGROUND OF THE INVENTION

Field of the Invention

The present invention relates generally to oral drug preparations including ethinylestradiol (EE) and cyproterone acetate (CPA) and more specifically to alternative dosing schedules using such preparations.

Background Information

Polycystic ovary syndrome (PCOS) is a common hormonal disorder characterized by menstrual irregularity, acne, hirsutism, and infertility, among other symptoms. Increased testosterone concentrations, elevated luteinizing hormone, insulin resistance, lipid-profile changes, and polycystic ovaries in ultrasound scans are biochemical and ultrasound features associated with the syndrome. Women with PCOS may be at risk for other serious health problems, such as type 2 diabetes, high blood pressure, heart disease, and uterine cancer. Although there is no known cure for PCOS, symptoms are managed with changes in diet and exercise, diabetes medications, and hormonal contraceptives.

CPA is a potent progestogen and anti-androgen that blocks the binding of dihydrotestosterone to its receptor, reducing 5-α reductase activity and impairing androgen synthesis. Cyproterone acetate (CPA) has been available outside the U.S. for many years as either a component of combination oral contraceptive pills (OCP) or as a stand-alone anti-androgen compound. CPA is an antiandrogen and a progesterone. Its principal advantage compared to other progesterone used in the combination birth control pills is its anti-androgen properties that can be used to treat hyperandrogenic conditions such as polycystic ovary syndrome (PCOS), acne and excessive hair growth in women.

The most commonly available combination OCPs containing CPA contains ethinylestradiol (EE) 35 µg and CPA 2 mg. The product is typically taken once daily for 21 days, followed by a 7-day free interval. It is indicated for the treatment of women with severe acne, with associated symptoms of androgenization, including seborrhea and mild hirsutism. In addition, it is widely prescribed as a contraceptive on an off-label basis. However, this dosing regimen has been associated with deaths from venous thromboembolism (VTE). The VTE risk is affected not only by the type of progestin combined with the estrogen, but also by estrogen dosage.

SUMMARY OF THE INVENTION

The present invention is based on the discovery that oral drug preparations including a progestin such as cyproterone acetate (CPA) can be used as an antiandrogen and to provide female contraception without affecting the efficacy of CPA, while reducing the risk of venous thromboembolism VTE, particularly when used in novel dosing schedules as described herein. The present invention generally relates to a triphasic oral drug regimen using ethinylestradiol (EE) and a progestin, such as cyproterone acetate (CPA). The triphasic regimen includes a loading phase, a maintenance phase and a resting phase. It should be understood that while CPA is an illustrative example, other progestin compounds may be used in the oral preparations and dosing schedules described herein. In one aspect, the oral preparations disclosed herein are provided to females of child-bearing age.

In one embodiment, the present invention provides an oral drug preparation including (a) a first composition including about 5 to 50 µg ethinylestradiol (EE) and about 1 to 10 mg of a progestin, for example, cyproterone acetate (CPA); and (b) a second composition including about 1 to 10 mg progestin, for example, CPA.

In one aspect, the first composition includes about 35 µg EE and about 2 mg CPA. In another aspect, the second composition includes about 2 mg CPA. In one aspect, beginning on day 15 of a dosing schedule, the second composition is administered on day 15 and then every other day. In another aspect, the first composition is administered to the subject daily beginning on day 1 of the dosing schedule and for 14 consecutive days, inclusive, and every other day beginning on day 16 of the dosing schedule. In some aspects, the dosing schedule is about 84 days. In other aspects, the preparation further includes a third composition including no active ingredient. In some aspects, beginning the day following the last day of the dosing schedule, the third composition with no active ingredient is administered daily for 4 to 7 consecutive days, inclusive.

In another embodiment, the invention provides an oral drug preparation including (a) a first composition including about 5 to 50 µg ethinylestradiol (EE) and about 1 to 10 mg cyproterone acetate (CPA); and (b) a second composition including about 1 to 10 mg CPA.

In one aspect, the first composition includes about 35 µg EE and about 2 mg CPA. In another aspect, the second composition includes about 2 mg CPA. In one aspect, beginning on day 8 of a dosing schedule, the second composition is administered on day 8 and then every other day. In one aspect, beginning on day 1 of the dosing schedule, the first composition is administered on day 1 and then every other day. In some aspects, beginning on day 2 of the dosing schedule, the second composition is further administered on day 2 and then every other day. In another aspect, the first composition is administered to the subject daily beginning on day 1 of the dosing schedule and for 7 consecutive days, inclusive, and every other day beginning on day 9 of the dosing schedule. In various aspects, the dosing schedule includes 21, 28, 49 or 84 days. In some aspects, the preparation further includes a third composition including no active ingredient. In various aspects, beginning the day following the last day of the dosing schedule, the third composition with no active ingredient is administered daily for 4 to 7 consecutive days, inclusive.

In an additional embodiment, the invention provides an oral drug preparation including a) a first composition including about 5 to 50 µg ethinylestradiol (EE) and about 1 to 10 mg cyproterone acetate (CPA); and b) a second composition including about 5 to 50 µg ethinylestradiol (EE) and about 1 to 10 mg cyproterone acetate (CPA); wherein the second composition includes a lower amount of EE as compared to the first composition.

In one aspect, the first composition includes about 35 µg EE and about 2 mg CPA. In another aspect, the second composition includes about 15 μg EE and about 2 mg CPA. In one aspect, the first and second compositions are administered to a subject on alternating days on a 30-day dosing schedule. In some aspects, the first composition is administered on day 1 of the 30-day dosing schedule.

In one embodiment, the invention provides a method of treating one or more symptoms of hyperandrogenic conditions or hyperandrogenic activities in a subject including administering to the subject an oral drug preparation including (a) a first composition including about 5 to 50 μg ethinylestradiol (EE) and about 1 to 10 mg cyproterone acetate (CPA); and (b) a second composition including about 1 to 10 mg CPA, wherein beginning on day 15 of a dosing schedule, the second composition is administered on day 15 and then every other day, thereby treating one or more symptoms of hyperandrogenic conditions or hyperandrogenic activities in the subject.

In one aspect, the first composition includes about 35 μg EE and about 2 mg CPA and the second composition includes about 2 mg CPA. In another aspect, the first composition is administered to the subject daily beginning on day 1 of the dosing schedule and for 14 consecutive days, inclusive, and every other day beginning on day 16 of the dosing schedule. In one aspect, the method further includes, beginning the day following the last day of the dosing schedule, administering to the subject a third composition including no active ingredient. In one aspect, the one or more symptoms of hyperandrogenic conditions or hyperandrogenic activities is selected from the group consisting of polycystic ovary syndrome (PCOS), acne, severe acne, seborrhea, mild hirsutism and excessive hair growth. In another aspect, administering the preparation further provides contraception to the subject. In one aspect, administering the preparation further reduces a risk of vascular thromboembolism (VTE) in the subject.

In another embodiment, the invention provides a method of treating one or more symptoms of hyperandrogenic conditions or hyperandrogenic activities in a subject including administering to the subject an oral drug preparation including (a) a first composition including about 5 to 50 μg ethinylestradiol (EE) and about 1 to 10 mg cyproterone acetate (CPA); and (b) a second composition including about 1 to 10 mg CPA, wherein beginning on day 8 of a dosing schedule, the second composition is administered on day 8 and then every other day thereby treating one or more symptoms of hyperandrogenic conditions or hyperandrogenic activities in the subject.

In one aspect, beginning on day 1 of the dosing schedule, the first composition is administered on day 1 and then every other day, and beginning on day 2 of the dosing schedule, the second composition is further administered on day 2 and then every other day. In another aspect, the first composition is administered to the subject daily beginning on day 1 of the dosing schedule and for 7 consecutive days, inclusive, and every other day beginning on day 9 of the dosing schedule.

In an additional embodiment, the invention provides a method of treating one or more symptoms of hyperandrogenic conditions or hyperandrogenic activities in a subject including administering to the subject an oral drug preparation including a) a first composition including about 5 to 50 μg ethinylestradiol (EE) and about 1 to 10 mg cyproterone acetate (CPA); and b) a second composition including about 5 to 50 μg ethinylestradiol (EE) and about 1 to 10 mg cyproterone acetate (CPA); wherein the second composition includes a lower amount of EE as compared to the first composition, thereby treating one or more symptoms of hyperandrogenic conditions or hyperandrogenic activities in the subject.

In another embodiment, the invention provides a pharmaceutical package including an oral preparation as disclosed herein. In one aspect, the pharmaceutical package includes instructions for administration of or ingestion of the oral preparation.

BRIEF DESCRIPTION OF THE DRAWINGS

FIG. 1A illustrates simulated EE plasma concentrations at day 14. FIG. 1B illustrates EE plasma concentrations at days 83 and 84. Solid line is the mean and shaded area is the 90% prediction interval for 1000 simulated EE concentration vs time profiles.

FIG. 2A illustrates simulated EE plasma concentrations at day 14. FIG. 2B illustrates EE plasma concentrations at days 83 and 84. Solid line is the mean and shaded area is the 90% prediction interval for 1000 simulated EE concentration vs time profiles.

DETAILED DESCRIPTION OF THE INVENTION

Figure 1A:
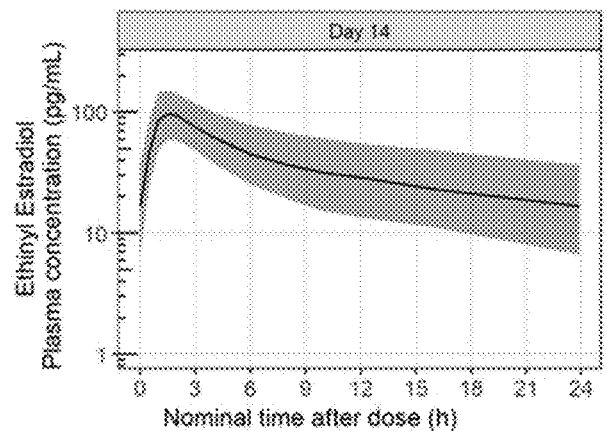
FIGS. 1A-1B illustrate simulated EE plasma concentrations of a dosing regimen including 35 μg EE daily from day 1 to 14 and 35 μg EE every other day from day 15 to 84.

The present invention is based on the discovery that alternative dosing of ethinylestradiol and cyproterone acetate (CPA) can reduce venous thromboembolism (VTE) risks but maintain the efficacy of CPA as an antiandrogen and oral contraceptive.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The present invention generally relates to a triphasic oral drug regimen using ethinylestradiol (EE) and a progestin such as cyproterone acetate (CPA). The triphasic regimen includes a loading phase, a maintenance phase and a resting phase.

The loading phase aims to change the hormonal profile of a subject to provide hormonal contraception. By maintaining estrogen levels high, the loading phase provides the prevention of ovulation in the subject. During the loading phase, which includes from 0 to 14 days, a combination of EE and CPA is administered to the subject daily. For example, the loading phase can last 0, 7 or 14 days. During the loading phase, a composition including 5-50 µg EE and 1-10 mg progestin, such as CPA, can be administered daily to the subject. For example, the composition includes 35 µg EE and 2 mg CPA.

The maintenance phase aims at maintaining the prevention of a pregnancy in the subject by suppressing androgen hormones via a sustained administration of a progestin, while limiting the administered EE dose. During the maintenance phase, which includes from 21 to 84 days, two drugs are administered on an alternate schedule, such that progestin is administered daily, and EE is either administered every other day or daily with a reduced dose every other day. For example, a first composition includes EE and CPA, while a second composition include CPA only; or a first composition includes a higher dose of EE and CPA while a second composition includes a lower dose of EE and CPA. For example, the maintenance phase can last 21, 28, 30, 49 or 84 days. During the maintenance phase, a first composition including 5-50 µg EE and 1-10 mg CPA, and a second composition including 0-50 µg EE and 1-10 mg CPA can be administered on an alternate schedule to a subject. For example, the first composition includes 35 µg EE and 2 mg CPA and the second composition includes 2 mg CPA, each composition being administered every other day to the subject. Alternatively, the first composition includes 35 µg EE and 2 mg CPA and the second composition includes 15 µg EE and 2 mg CPA, each composition being administered every other day to the subject.

The resting phase, which is an inactive phase, aims at allowing a menstrual discharge. During the resting phase, which includes from 0 to 7 days, no drug preparation, or a drug preparation that does not include any active ingredient (e.g., no EE and no CPA) is administered to the subject. By way of example, a resting phase can last 0, 4 or 7 days.

The present disclosure describes several illustrative examples of such dosing regimens (see regimens 1-5 below) but is not meant to be restricted to those 5 regimens alone.

Without wanting to be bound by a particular theory, it is believed that the triphasic oral drug regimens disclosed herein reduce estrogen exposure in the subject by increasing the dosing interval, which allows the oral drugs to be an efficient birth control pill, while reducing estrogen exposure, which may reduce the risk of venous thromboembolism (VTE) or other side effects associated with the administration of estrogen.

In one embodiment, the present invention provides an oral drug preparation including a first composition including about 5 to 50 µg ethinylestradiol (EE) and about 1 to 10 mg progestin (e.g., CPA); and a second composition including about 1 to 10 mg progestin (e.g., CPA), wherein beginning on day 15 of a dosing schedule, the second composition is administered on day 15 and then every other day.

Ethinylestradiol (EE) is an estrogen medication widely used in birth control pills in combination with progestins. EE is usually taken by mouth but is also used as a patch and vaginal ring. EE is an estrogen, or an agonist of the estrogen receptors, the biological target of estrogens like estradiol. It is a synthetic derivative of the natural estrogen estradiol and differs from it in various ways. Compared to estradiol, EE has greatly improved bioavailability when taken by mouth, is more resistant to metabolism, and shows relatively increased effects in certain parts of the body such as the liver and uterus. These differences make EE more favorable for use in birth control pills than estradiol, though it is associated with an increased risk of blood clots and certain other rare adverse effects.

The drug preparation of the present invention includes about 5 to 50 µg EE. For example, the drug composition includes about 5, 6, 7, 8, 9, 10, 15, 20, 25, 30, 35, 40, 45, or 50 µg EE. While the illustrative dosing regimens provided herein are simply illustrative, it should be understood that EE and progestin can vary, however, it is preferred in some instances to achieve a daily average of 20 µg EE. Further, in some illustrative examples, the first 7 or 14 days should be an induction using the higher strength pills, the last 7 days should be inactive to allow a discharge, and other days in between should alternate between high or low strength pills to limit the intake of EE and reduce VTE risk, for example.

Progestogens are a type of medication which produce effects similar to those of the natural female sex hormone progesterone. The term "progestin" as used herein is meant to refer to a synthetic progestogen however the terms may be used interchangeably herein. Progestogens and progestins are used most commonly in hormonal birth control and menopausal hormone therapy but can also be used in the treatment of gynecological conditions, to support fertility and pregnancy, to lower sex hormone levels for various purposes, and for other indications. Progestogens and progestins can be used alone or in combination with estrogens and are available in a wide variety of formulations and for use by many different routes of administration. Non-limiting examples of progestogens and progestins include natural or bioidentical progesterone, acetomepregenol, algestone acetophenide, allylestrenol, altrenogest, chlormadinone acetate, cyproterone acetate, danazol, delmadinone acetate, desogestrel, dienogest, drospirenone, dydrogesterone, etonogestrel, etynodiol diacetate, flugestone acetate, gestodene, gestonorone caproate, gestrinone, hydroxyprogesterone caproate, levonorgestrel, lynestrenol, medrogestone, medroxyprogesterone acetate, megestrol acetate, melengestrol acetate, nomegestrol acetate, norelgestromin, norethisterone, norethisterone acetate, norethisterone enanthate, norgestimate, norgestomet, norgestrel, normethandrone, osaterone acetate, oxendolone, progesterone, proligestone, promegestone, segesterone acetate, tibolone and trimegestone.

In one aspect, the progestin is cyproterone acetate (CPA).

Cyproterone acetate (CPA) is an antiandrogen and progestin medication used in the treatment of androgen-dependent conditions like acne, excessive hair growth, early puberty, and prostate cancer, as a component of feminizing hormone therapy for transgender women, and in birth control pills. It is formulated and used both alone and in combination with an estrogen and is available for use both by mouth and by injection into muscle. CPA is taken by mouth one to three times per day or given by injection once or twice per week. CPA is used as a progestin and antiandrogen in hormonal birth control and in the treatment of androgen-dependent conditions. Specifically, CPA is used in combined birth control pills, in the treatment of androgen-dependent skin and hair conditions such as acne, seborrhea, excessive hair growth, and scalp hair loss, high androgen levels, in transgender hormone therapy, to treat prostate cancer, to reduce sex drive in sex offenders or men with paraphilias or hypersexuality, to treat early puberty, and for other uses. It is used both at low doses and at higher doses.

The drug preparation of the present invention includes about 1 to 10 mg CPA. For example, the drug composition includes about 1, 2, 3, 4, 5, 6, 7, 8, 9, or 10 mg CPA.

In one aspect, the first composition includes about 35 µg EE and about 2 mg CPA. In another aspect, the second composition includes about 2 mg CPA.

As used herein, the phrase "dosing schedule" refers to the schedule that can be followed for the administration of the compositions of the drug preparation described herein. The entire dosing schedule can be determined as between a 21-day dosing schedule and a 84-day dosing schedule, which provides that the drug preparations of the present invention are administered during between 21 and 84 consecutive days. In some aspects, the dosing schedule includes 21, 28, 30, 49 or 84 days. In one aspect, the dosing schedule is about 84 days.

In some aspects, beginning on day 15 of a dosing schedule, the second composition is administered on day 15 and then every other day.

By "every other day", it is meant that the composition is administered successively on "alternating days" starting on a given day, and during a given time period of dosing schedule. For example, the second composition, that is administered on day 15 is not administered on day 16, but is rather then administered on days 17, 19 and 21 of a 21-day dosing schedule; on days 17, 19, 21, 23, 25 and 27 of a 28-day dosing schedule; on days 17, 19, 21, 23, 25, 27, and 29 of a 30-day dosing schedule; on days 17, 19, 21, 23, 25, 27, 29, 31, 33, 35, 37, 39, 41, 43, 45, 47 and 49 of a 49-day dosing schedule; or on days 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81 and 83 of a 84-day dosing schedule, etc.

In other aspects, the first composition is administered to the subject daily beginning on day 1 of the dosing schedule and for 14 consecutive days, inclusive, and every other day beginning on day 16 of the dosing schedule.

For example, the first composition can be administered on days 1, 2, 3, 4, 5, 6, 7, 8, 9, 10, 11, 12, 13, 14, 16, 18 and 20 of a 21-day dosing schedule, on days 1, 2, 3, 4, 5, 6, 7, 8, 9, 10, 11, 12, 13, 14, 16, 18, 20, 22, 24, 26 and 28 of a 28-day dosing schedule, on days 1, 2, 3, 4, 5, 6, 7, 8, 9, 10, 11, 12, 13, 14, 16, 18, 20, 22, 24, 26, 28 and 30 of a 30-day dosing schedule, on days 1, 2, 3, 4, 5, 6, 7, 8, 9, 10, 11, 12, 13, 14, 16, 18, 20, 22, 24, 26, 28, 30, 32, 34, 36, 38, 40, 42, 44, 46 and 48 of a 49-day dosing schedule, or on days 1, 2, 3, 4, 5, 6, 7, 8, 9, 10, 11, 12, 13, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82 and 84 of a 84-day dosing schedule and so on. Accordingly, the second composition is not administered from day 1 to day 14 of the dosing schedule.

In other aspects, the drug preparation further includes a third composition including no active ingredient.

By "no active ingredient", it is meant that the ingredients included in the third composition do no produce any therapeutic or physiological effect in a subject upon administration. For example, and as opposed to the first and second composition, the third composition does not include EE or progestin.

In one aspect, beginning the day following the last day of the active ingredient dosing schedule, the third composition is administered daily for 4 to 7 consecutive days, inclusive.

The dosing schedule can optionally be followed by a period of time during which no drug preparation is administered (e.g., a drug free interval), followed by a subsequent new dosing schedule. During the drug-free interval, a composition including no active ingredient is administered (e.g., the third composition), to help the subject maintain compliance with daily administration of a drug preparation. Alternatively, the initial dosing schedule can be directly followed by a new dosing schedule. In both cases, the new subsequent dosing schedule is generally the repetition of the initial dosing schedule for an additional dosing period of 21-84 days. The successive dosing schedules can be repeated as long as the effects sought after by the oral drug are desired. The drug free interval can for example be a 4-day period or a 7-day period during which no drug preparation is administered, or a placebo drug preparation, including no active component (e.g., no EE and no progestin). The dosing schedule is generally 21-84 days, but other length of time can be applied. For example, the dosing schedule can be 21, 24, 28, 30, 49 or 84 days. The length of the drug-free interval can be determined based on the length of the dosing schedule.

For example, for dosing schedules of 21 or 24 days, the drug-free interval is usually a 4-day period during which no drug preparation is administered (or a placebo preparation including no active component). For dosing schedules of 28, 30, 49 or 84 days, the drug-free interval is usually a 7-day period during which no drug preparation is administered (or a placebo preparation including no active component).

For example, the third composition can be administered on days 22, 23, 24 and 25 of a 21-day dosing schedule; on days 25, 26, 27 and 28 of a 24-day dosing schedule; on days 29, 30, 31, 32, 33, 34 and 35 of a 28-day dosing schedule; on days 31, 32, 33, 34, 35, 36 and 37 of a 30-day dosing schedule; on days 50, 51, 52, 53, 54, 55 and 56 of a 49-day dosing schedule; or on days 85, 86, 87, 88, 89, 90 and 91 of a 84-day dosing schedule, etc.

In another embodiment, the present invention provides an oral drug preparation including a first composition including about 5 to 50 µg EE and about 1 to 10 mg progestin; and a second composition including about 1 to 10 mg progestin, wherein beginning on day 8 of a dosing schedule, the second composition is administered on day 8 and then every other day.

In one aspect, the progestin is CPA.

In one aspect, the first composition includes about 35 µg EE and about 2 mg CPA. In another aspect, the second composition includes about 2 mg CPA.

In various aspects, the dosing schedule includes 21, 28, 30, 49 or 84 days. In one aspect, the dosing schedule is about 30 days.

In some aspects, the second composition as described herein can be administered every other day starting from day 8 and until the end of the dosing schedule.

For example, the composition is administered on day 8, and is not administered on day 9, but is rather then administered on days 10, 12, 14, 16, 18 and 20 of a 21-day dosing schedule; on days 10, 12, 14, 16, 18, 20, 22, 24, 26 and 28 of a 30-day dosing schedule; on days 10, 12, 14, 16, 18, 20, 22, 24, 26, 28 and 30 of a 30-day dosing schedule; on days 10, 12, 14, 16, 18, 20, 22, 24, 26, 28, 30, 32, 34, 36, 38, 40, 42, 44, 46 and 48 of a 49-day dosing schedule; or on days 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82 and 84 of a 84-day dosing schedule, etc.

In another aspect, the first composition is administered to the subject daily beginning on day 1 of a dosing schedule and for 7 consecutive days, inclusive, and every other day beginning on day 9 of the dosing schedule.

In some aspects, the first composition of the drug preparation can be administered daily from day 1 to day 7. For example, the first composition can be administered on days 1, 2, 3, 4, 5, 6, 7, 9, 11, 13, 15, 17, 19 and 21 of a 21-day dosing schedule, on days 1, 2, 3, 4, 5, 6, 7, 9, 11, 13, 15, 17, 19, 21, 23, 25, and 27 of a 28-day dosing schedule, on days 1, 2, 3, 4, 5, 6, 7, 9, 11, 13, 15, 17, 19, 21, 23, 25, 27, and 29 of a 30-day dosing schedule, on days 1, 2, 3, 4, 5, 6, 7, 9, 11, 13, 15, 17, 19, 21, 23, 25, 27, 29, 31, 33, 35, 37, 39, 41, 43, 45, 47, and 49 of a 49-day dosing schedule, or on days 1, 2, 3, 4, 5, 6, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81 and 83 of a 84-day dosing schedule. Accordingly, the second composition is not administered from day 1 to day 7 of the dosing schedule.

In other aspects, the drug preparation further includes a third composition including no active ingredient. In one aspect, beginning the day following the last day of the dosing schedule, the third composition is administered daily for 7 consecutive days, inclusive.

In another embodiment, the present invention provides an oral drug preparation including a first composition including about 5 to 50 µg EE and about 1 to 10 mg progestin; and a second composition including about 1 to 10 mg progestin, wherein beginning on day 8 of a dosing schedule, the second composition is administered on day 8 and then every other day.

In one aspect, beginning on day 1 of a dosing schedule, the first composition is administered every other day.

For example, the first composition that is administered on day 1 is not administered on day 2, but is rather then administered on days 3, 5, 7, 9, 11, 12, 13, 15, 17, 19 and 21 of a 21-day dosing schedule; on days, 3, 5, 7, 9, 11, 12, 13, 15, 17, 19, 21, 23, 25 and 27 of a 30-day dosing schedule; on days, 3, 5, 7, 9, 11, 12, 13, 15, 17, 19, 21, 23, 25, 27 and 29 of a 30-day dosing schedule; on days 3, 5, 7, 9, 11, 12, 13, 15, 17, 19, 21, 23, 25, 27, 29, 31, 33, 35, 37, 39, 41, 43, 45, 47 and 49 of a 49-day dosing schedule; or on days 3, 5, 7, 9, 11, 12, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81 and 83 of a 84-day dosing schedule, etc.

In some aspects, beginning on day 2 of a dosing schedule, the second composition is further administered every other day. Accordingly, the second is additionally administered every other day from day 2 to day 8 (e.g., the second composition is additionally administered on day 2, 4 and 6 of the dosing schedule).

For example, the second composition that is administered on day 2 is no administered on day 3, but is rather then administered on days 4, 6, 8, 10, 12, 14, 16, 18 and 20 of a 21-day dosing schedule; on days 4, 6, 8, 10, 12, 14, 16, 18, 20, 22, 24, 26 and 28 of a 30-day dosing schedule; on days 4, 6, 8, 10, 12, 14, 16, 18, 20, 22, 24, 26, 28 and 30 of a 30-day dosing schedule; on days 4, 6, 8, 10, 12, 14, 16, 18, 20, 22, 24, 26, 28, 30, 32, 34, 36, 38, 40, 42, 44, 46 and 48 of a 49-day dosing schedule; or on days 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82 and 84 of a 84-day dosing schedule, etc.

In one aspect, the progestin is CPA.

In one aspect, the first composition includes about 35 µg EE and about 2 mg CPA. In another aspect, the second composition includes about 2 mg CPA.

In various aspects, the dosing schedule includes 21, 30, 49 or 84 days. In one aspect, the dosing schedule is about 30 days. In another aspect, the dosing schedule is about 84 days.

In another embodiment, the invention provides an oral drug preparation including a first composition including about 5 to 50 µg ethinylestradiol (EE) and about 1 to 10 mg progestin; and a second composition including about 5 to 50 µg EE and about 1 to 10 mg progestin; wherein the second composition includes a lower amount of EE as compared to the first composition, and wherein the first and second compositions are administered to a subject on alternating days on a 30-day dosing schedule. In one aspect, the progestin is CPA.

By "alternating days" it is meant that the first and the second compositions are successively alternated during the 30 days of the dosing schedule; therefore, the composition that is administered on day 1 is not administered on day 2, but is rather then administered on days 3, 5, 7, 9, 11, 12, 13, 15, 17, 19, 21, 23, 25, 27 and 29 of a 30-day schedule. The composition that is administered on day 2 is no administered on day 3, but is rather then administered on days 4, 6, 8, 10, 12, 14, 16, 18, 20, 22, 24, 26, 28 and 30 of a 30-day schedule.

In one aspect, the first composition is administered on day 1, and then every other day of the 30-day dosing schedule. Accordingly, the second composition is not administered on day 1, but rather on day 2, and then every other day of the 30-day dosing schedule.

By "lower amount" it is meant that the amount of EE in the first composition, can be any amount of EE ranging from 5 to 50 mg, with the proviso that the amount of EE in the second composition is less than the amount in the first composition.

In one aspect, the first composition includes about 35 µg EE and about 2 mg CPA; and a second composition including about 15 µg EE and about 2 mg CPA.

The dosing schedules described herein are preferably administered at the same or similar time each day, regardless of the composition of the drug preparation.

In an additional embodiment, the invention provides a method of treating one or more symptoms of hyperandrogenic conditions or hyperandrogenic activities in a subject including administering to the subject any of the preparations described herein.

The term "subject" as used herein refers to any individual or patient to which the subject methods are performed. Generally, the subject is human, although as will be appreciated by those in the art, the subject may be an animal. In a preferred aspect, the subject is a woman.

By treating, it is meant that the subject is administered a "treatment", a term used interchangeably herein with the term "therapeutic method" and which refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures). The oral drug preparations of the present invention can be administered, which should be understood as providing a drug preparation in a therapeutically effective amount to the subject in need of treatment. Suitable unit dosage forms include, but are not limited to powders, tablets, pills, and capsules. For the preferred oral administration, tablets, caplets, gel-caps, soft capsules, capsules, pills, suspensions or solutions are particularly suitable; for parenteral application, oily solutions such as, for example, sesame oil or castor oil solutions which can optionally additionally contain a diluent such as, for example, benzyl benzoate or benzyl alcohol. For preferred transdermal applications, skin patches placed on the skin to deliver a time released dose of medication through the skin and into the blood stream are desirable. Types of patches include single-layer drug-in-adhesive, multi-layer drug-in-adhesive, reservoir, microstructured transdermal systems (MTS) and matrix types. The main components to a transdermal patch are the liner, which protects the patch during storage and is generally removed prior to use; a drug, which is typically stored in solution in direct contact with the release liner; adhesive, which serves to adhere the components of the patch together along with adhering the patch to the skin; a membrane, which controls the release of the drug from the reservoir in single- and multi-layer patches; and backing, which protects the patch from the outer environment.

In one aspect, the method includes the administration of an oral drug composition including a first composition including about 5 to 50 µg EE and about 1 to 10 mg progestin; and a second composition including about 1 to 10 mg progestin, wherein beginning on day 15 of a dosing schedule, the second composition is administered on day 15 and then every other day. In another aspect, the first composition is administered to the subject daily beginning on day 1 of the dosing schedule for 14 consecutive days, inclusive, and every other day beginning on day 16 of the dosing schedule. Accordingly, from day 1 to day 14, inclusive, the second composition is not administered. For example, the progestin can be CPA. In one aspect, the first composition includes about 35 µg EE and about 2 mg CPA and the second composition includes about 2 mg CPA.

In another aspect, the first composition includes about 5 to 50 µg EE and about 1 to 10 mg progestin and the second composition includes about 1 to 10 mg progestin, wherein beginning on day 1 of the dosing schedule, the first composition is administered on day 1 and then every other day and beginning on day 2 of the dosing schedule, the second composition is further administered on day 2 and then every other day. In one aspect, the progestin is CPA. In one aspect, the first composition includes about 35 µg EE and about 2 mg CPA and the second composition includes about 2 mg CPA.

In an additional aspect, the first composition includes about 5 to 50 µg EE and about 1 to 10 mg progestin and the second composition includes about 1 to 10 mg progestin, wherein the first composition is administered to the subject daily beginning on day 1 of the dosing schedule, and for 7 consecutive days, inclusive, and every other day beginning on day 9 of the dosing schedule. Accordingly, from day 1 to day 7, inclusive, the second composition is not administered. In one aspect, the progestin is CPA. In one aspect, the first composition includes about 35 µg EE and about 2 mg CPA and the second composition includes about 2 mg CPA.

In a further aspect, the first composition includes about 5 to 50 µg EE and about 1 to 10 mg progestin; and the second composition includes about 5 to 50 µg EE and about 1 to 10 mg progestin; wherein the second composition includes a lower amount of EE as compared to the first composition, and wherein the first and second compositions are administered to a subject on alternating days on a 30-day dosing schedule. In one aspect, the progestin is CPA. In one aspect, the first composition includes about 35 µg EE and about 2 mg CPA and the second composition includes about 15 µg EE and about 2 mg CPA.

In one aspect, the preparation is administered over a 30-day administration period. In another aspect, the preparation is administered over a 84-day administration period.

In some aspects, the method further includes administering a third composition including no active ingredient. In some aspects, beginning the day following the last day of the dosing schedule, the third composition is administered daily for 7 consecutive days, inclusive.

In another aspect, the one or more symptoms of hyperandrogenic conditions or hyperandrogenic activities is selected from the group consisting of polycystic ovary syndrome (PCOS), acne, severe acne, seborrhea, mild hirsutism and excessive hair growth.

As used herein, the phrases "hyperandrogenic conditions" and/or "hyperandrogenic activities" are meant to refer to the symptoms of hyperandrogenism. Hyperandrogenism is a medical condition characterized by high levels of androgens in females. Symptoms may include acne, seborrhea (inflamed skin), hair loss on the scalp, increased body or facial hair, and infrequent or absent menstruation. Hyperandrogenism is caused in about 70% of cases by polycystic ovary syndrome (PCOS). Other causes include adrenal hyperplasia, Cushing's disease, certain types of cancers, and certain medications.

Polycystic ovary syndrome (PCOS), is a set of symptoms observed in females, and due to elevated androgens. Polycystic ovaries develop when the ovaries are stimulated to produce excessive amounts of androgenic hormones, in particular testosterone, by either the release of excessive luteinizing hormone (LH) by the anterior pituitary gland, through high levels of insulin in the blood (hyperinsulinemia) in women whose ovaries are sensitive to this stimulus, and/or genetic susceptibility. Signs and symptoms of PCOS include irregular or no menstrual periods, heavy periods, excess body and facial hair (including mild hirsutism), acne (including severe acne), pelvic pain, difficulty getting pregnant, and patches of thick, darker, velvety skin. Conditions associated with PCOS include type 2 diabetes, obesity, obstructive sleep apnea, heart disease, mood disorders, and endometrial cancer.

In a further embodiment, the invention provides a method of providing contraception to a female subject including administering to the subject any of the preparations described herein.

As used herein, "providing contraception" refers to providing hormonal contraception to a female subject, as a method used to prevent pregnancy. Hormonal contraception includes combined oral contraceptive pills (OCP, containing both estrogen and a progestin). OCPs provide contraception by preventing fertilization mainly by inhibiting ovulation and thickening cervical mucus. They may also change the lining of the uterus and thus decrease implantation. Their effectiveness depends on the user's adherence to taking the pills. Combined oral contraceptives reduce the risk of ovarian cancer and endometrial cancer and do not change the risk of breast cancer. They often reduce menstrual bleeding and painful menstruation cramps. The lower doses of estrogen released from the vaginal ring may reduce the risk of breast tenderness, nausea, and headache associated with higher dose estrogen products.

In one aspect, the method includes the administration of an oral drug composition including a first composition including about 5 to 50 µg EE and about 1 to 10 mg progestin; and a second composition including about 1 to 10 mg progestin, wherein beginning on day 15 of a dosing schedule, the second composition is administered every other day. In another aspect, the first composition is administered to the subject daily beginning on day 1 of the dosing schedule for 14 consecutive days, inclusive, and every other day beginning on day 16 of the dosing schedule. Accordingly, from day 1 to day 14, inclusive, the second composition is not administered. For example, the progestin is CPA. In one aspect, the first composition includes about 35 µg EE and about 2 mg CPA and the second composition includes about 2 mg CPA.

In another aspect, the first composition includes about 5 to 50 µg EE and about 1 to 10 mg progestin and the second composition includes about 1 to 10 mg progestin, wherein beginning on day 1 of the dosing schedule, the first composition is administered on day 1 and then every other day and beginning on day 2 of the dosing schedule, the second composition is further administered on day 2 and then every other day. For example, the progestin is CPA. In one aspect, the first composition includes about 35 µg EE and about 2 mg CPA and the second composition includes about 2 mg CPA.

In an additional aspect, the first composition includes about 5 to 50 µg EE and about 1 to 10 mg progestin and the second composition includes about 1 to 10 mg progestin, wherein the first composition is administered to the subject daily beginning on day 1 of the dosing schedule, and for 7 consecutive days, inclusive, and every other day beginning on day 9 of the dosing schedule. Accordingly, from day 1 to day 7, inclusive, the second composition is not administered. For example, the progestin is CPA. In one aspect, the first composition includes about 35 µg EE and about 2 mg CPA and the second composition includes about 2 mg CPA.

In a further aspect, the first composition includes about 5 to 50 µg EE and about 1 to 10 mg progestin; and the second composition includes about 5 to 50 µg EE and about 1 to 10 mg progestin; wherein the second composition includes a lower amount of EE as compared to the first composition, and wherein the first and second compositions are administered to a subject on alternating days on a 30-day dosing schedule. For example, the progestin is CPA. In one aspect, the first composition includes about 35 µg EE and about 2 mg CPA and the second composition includes about 15 µg EE and about 2 mg CPA.

In another aspect, the preparation is administered over an 84-day administration period.

In some aspects, the method further includes administering a third composition including no active ingredient. In some aspects, beginning the day following the last day of the dosing schedule, the third composition is administered for 7 consecutive days, inclusive.

In one embodiment, the present invention provides a method of reducing a risk of vascular thromboembolism (VTE) in a subject including administering to the subject any of the preparations described herein.

Combined hormonal contraceptives are associated with a slightly increased risk of venous and arterial blood clots. A clot, or a piece of the clot, can break free and begin to travel around the body (e.g., an embolus), which can lead to venous or arterial thrombosis, which is responsible for congestion of the affected part of the body, and reduction of blood supply (which causes damage of the tissue, ischemia and necrosis). Complications can arise when a venous thromboembolism (commonly called a VTE) lodges in the lung as a pulmonary embolism, which may cause death.

All of the known OCPs have EE or another form estrogen in the active pills. These OCPs provide estrogen or its analogue every single day during the active pill period to suppress the hypothalamic-pituitary-ovarian axis and therefore ovulation. However, the dosage of estrogen required to achieve the suppression varies. In the U.S. the commonly used EE dosage in OCPs ranges from 10 to 30 µg. However, there are significant differences in the metabolism and serum concentrations of estrogen and related steroids in women treated with the same preparations. The mean oral bioavailability of EE is approximately 45%, with a large inter- and intraindividual variability. Owing to the large variability in EE bioavailability, EE levels produced by 35 µg EE in one woman may be similar to those generated by 50 µg in another woman. In addition, EE has a lower AUC and Cmax in obese women versus normal weight women, yet the observed PK differences did not translate into more ovarian follicular activity among obese women. The half-life of EE is 12 to 18 hours due to hepatic recirculation which means the acceptable dosing interval should be 24 to approximately 36 hours.

In contrast, the drug preparations of the present invention are designed to provide effective contraceptive pills, and efficient anti-androgen medication, while reducing the risk of vascular thromboembolism (VTE) usually associated with EE intake. The drug preparations of the present invention provide 5 independent regimens to limit the intake of EE, by reducing the overall EE intake, either by skipping the administration of EE on alternating days, or by reducing EE amount in the OCP on alternative days.

In one aspect, the method includes the administration of an oral drug composition including a first composition including about 5 to 50 µg EE and about 1 to 10 mg progestin; and a second composition including about 1 to 10 mg progestin, wherein beginning on day 15 of a dosing schedule, the second composition is administered every other day. In another aspect, the first composition is administered to the subject daily beginning on day 1 of the dosing schedule for 14 consecutive days, inclusive, and every other day beginning on day 16 of the dosing schedule. Accordingly, from day 1 to day 14, inclusive, the second composition is not administered. In another aspect, the preparation is administered over an 84-day administration period. For example, the progestin is CPA. In one aspect, the first composition includes about 35 µg EE and about 2 mg CPA and the second composition includes about 2 mg CPA.

In another aspect, the first composition includes about 5 to 50 µg EE and about 1 to 10 mg progestin and the second composition includes about 1 to 10 mg progestin, wherein beginning on day 1 of the dosing schedule, the first composition is administered on day 1 and then every other day and beginning on day 2 of the dosing schedule, the second composition is further administered on day 2 and then every other day. For example, the progestin is CPA. In one aspect, the first composition includes about 35 µg EE and about 2 mg CPA and the second composition includes about 2 mg CPA.

In an additional aspect, the first composition includes about 5 to 50 µg EE and about 1 to 10 mg progestin and the second composition includes about 1 to 10 mg progestin, wherein the first composition is administered daily beginning on day 1 of the dosing schedule, and for 7 consecutive days, inclusive, and every other day beginning on day 9 of the dosing schedule. Accordingly, from day 1 to day 7, inclusive, the second composition is not administered. For example, the progestin is CPA. In one aspect, the first composition includes about 35 µg EE and about 2 mg CPA and the second composition includes about 2 mg CPA.

In a further aspect, the first composition includes about 5 to 50 µg EE and about 1 to 10 mg progestin; and the second composition includes about 5 to 50 µg EE and about 1 to 10 mg progestin; wherein the second composition includes a lower amount of EE as compared to the first composition, and wherein the first and second compositions are administered to a subject on alternating days on a 30-day dosing schedule. For example, the progestin is CPA. In one aspect, the first composition includes about 35 µg EE and about 2 mg CPA and the second composition includes about 15 µg EE and about 2 mg CPA.

In some aspects, the method further includes administering a third composition including no active ingredient. In some aspects, beginning the day following the last day of the dosing schedule, the third composition is administered for 7 consecutive days, inclusive.

In the case of the preferred oral application, the oral preparations described herein are preferably packaged in the form of a pharmaceutical kit or package in which the daily dosages are arranged for proper sequential administration. This invention also relates, therefore, to a pharmaceutical unit which contains combination-type or separated medications such as: EE, progestin such as CPA, or EE-progestin, e.g., CPA, for example. The pharmaceutical units are provided in dosage units in a synchronized, fixed sequence, wherein the sequence or arrangement of the dosage units corresponds to the stages of daily administration as disclosed herein.

The pharmaceutical unit can be, for example, in the form of a transparent package ("blister pack") having dosage units arranged sequentially and consisting of the tablets for each phase, for example, dosage units containing in admixture with a pharmaceutically acceptable carrier, estrogen and/or CPA, followed by tablets for the inactive phase. In an illustrative example, a single capsule or tablet, for example, is to be taken each day over the period of the cycle. In the event a bi-daily co-administration is recommended, the above dosages can be halved. In one aspect, the pharmaceutical unit containing invention oral preparations include instructions for administration of or ingestion of the oral preparation by the user.

Presented below are examples discussing combination oral contraceptive pill and varying dosing regimen contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLE 1

Combination Oral Contraceptive Pills Dosing Regimens

To reduce the intake of ethinylestradiol (EE) without compromising the efficacy of a combination oral contraceptive pill (OCP) including cyproterone acetate (CPA) and EE, three independent dosing regimens have been developed (see Table 1).

The three exemplary dosing regimens are based on the alternate administration of two pills, having different EE and CPA content. The EE content in the pills is established at about 15 or 35 µg, and the CPA content is established at about 2 mg. However, in the three regimen, alternative dosages for CPA, varying between about 1-10 mg, and alternative dosages for EE varying between about 5-50 µg may be considered. In the three exemplary dosing regimens provided, the dosing schedule is established over a 30-day period. However, the regimen can be adjusted as needed to fit a 21-, 28-, 49-, or 84-days dosing schedule.

Dosing regimen 1 is based on the elimination of EE from the OCP every other day, which induces an overall reduction of the EE amount administered by half. In Regimen 1, a first pill includes EE 35 µg and CPA 2 mg, and a second pill includes CPA 2 mg. The regimen is designed to start on day 1 with a pill including EE 35 µg and CPA 2 mg, followed by a pill including only CPA (2 mg) on day 2. This schedule is designed to be repeated successively until the end of the 30-day period.

Dosing regimen 2 is based on the elimination of EE from the OCP every other day, after an initial week of administration without interruption. In Regimen 2, a first pill includes EE 35 µg and CPA 2 mg, and a second pill includes CPA 2 mg. The regimen is designed to start on day 1 with a pill including EE 35 µg and CPA 2 mg, which is administered daily from day 1 to day 7 inclusive. The initial 7-day period is followed by the administration of a pill including only CPA (2 mg) on day 8, which is followed by the administration of a pill including EE 35 µg and CPA 2 mg. This alternate administration is designed to be repeated successively until the end of the 30-day period (e.g., from day 8 to day 30).

Dosing regimen 3 is based on the reduction of EE from the OCP every other day, by alternating pills including varying amount of EE. In Regimen 1, a first pill includes EE 35 µg and CPA 2 mg, and a second pill includes EE 15 µg and CPA 2 mg. The regimen is designed to start on day 1 with a pill including EE 35 µg and CPA 2 mg, followed by a pill including only EE 15 µg and CPA 2 mg on day 2. This schedule is designed to be repeated successively until the end of the 30-day period.

TABLE 1

Dosing regimens 1-3 summary

| | Sample Regimen 1 | Sample Regimen 2 | Sample Regimen 3 |
|---|---|---|---|
| Day 1 | EE 35 µg and CPA 2 mg | EE 35 µg and CPA 2 mg | EE 35 µg and CPA 2 mg |
| Day 2 | CPA 2 mg | EE 35 µg and CPA 2 mg | EE 15 µg and CPA 2 mg |
| Day 3 | EE 35 µg and CPA 2 mg | EE 35 µg and CPA 2 mg | EE 35 µg and CPA 2 mg |
| Day 4 | CPA 2 mg | EE 35 µg and CPA 2 mg | EE 15 µg and CPA 2 mg |
| Day 5 | EE 35 µg and CPA 2 mg | EE 35 µg and CPA 2 mg | EE 35 µg and CPA 2 mg |
| Day 6 | CPA 2 mg | EE 35 µg and CPA 2 mg | EE 15 µg and CPA 2 mg |
| Day 7 | EE 35 µg and CPA 2 mg | EE 35 µg and CPA 2 mg | EE 35 µg and CPA 2 mg |
| Day 8 | CPA 2 mg | CPA 2 mg | EE 15 µg and CPA 2 mg |
| Day 9 | EE 35 µg and CPA 2 mg | EE 35 µg and CPA 2 mg | EE 35 µg and CPA 2 mg |
| Day 10 | CPA 2 mg | CPA 2 mg | EE 15 µg and CPA 2 mg |
| Day 11 | EE 35 µg and CPA 2 mg | EE 35 µg and CPA 2 mg | EE 35 µg and CPA 2 mg |
| Day 12 | CPA 2 mg | CPA 2 mg | EE 15 µg and CPA 2 mg |
| Day 13 | EE 35 µg and CPA 2 mg | EE 35 µg and CPA 2 mg | EE 35 µg and CPA 2 mg |
| Day 14 | CPA 2 mg | CPA 2 mg | EE 15 µg and CPA 2 mg |
| Day 15 | EE 35 µg and CPA 2 mg | EE 35 µg and CPA 2 mg | EE 35 µg and CPA 2 mg |
| Day 16 | CPA 2 mg | CPA 2 mg | EE 15 µg and CPA 2 mg |

TABLE 1-continued

Dosing regimens 1-3 summary

| | Sample Regimen 1 | Sample Regimen 2 | Sample Regimen 3 |
|---|---|---|---|
| Day 17 | EE 35 µg and CPA 2 mg | EE 35 µg and CPA 2 mg | EE 35 µg and CPA 2 mg |
| Day 18 | CPA 2 mg | CPA 2 mg | EE 15 µg and CPA 2 mg |
| Day 19 | EE 35 µg and CPA 2 mg | EE 35 µg and CPA 2 mg | EE 35 µg and CPA 2 mg |
| Day 20 | CPA 2 mg | CPA 2 mg | EE 15 µg and CPA 2 mg |
| Day 21 | EE 35 µg and CPA 2 mg | EE 35 µg and CPA 2 mg | EE 35 µg and CPA 2 mg |
| Day 21 | CPA 2 mg | CPA 2 mg | EE 15 µg and CPA 2 mg |
| Day 23 | EE 35 µg and CPA 2 mg | EE 35 µg and CPA 2 mg | EE 35 µg and CPA 2 mg |
| Day 24 | CPA 2 mg | CPA 2 mg | EE 15 µg and CPA 2 mg |
| Day 25 | EE 35 µg and CPA 2 mg | EE 35 µg and CPA 2 mg | EE 35 µg and CPA 2 mg |
| Day 26 | CPA 2 mg | CPA 2 mg | EE 15 µg and CPA 2 mg |
| Day 27 | EE 35 µg and CPA 2 mg | EE 35 µg and CPA 2 mg | EE 35 µg and CPA 2 mg |
| Day 28 | CPA 2 mg | CPA 2 mg | EE 15 µg and CPA 2 mg |
| Day 29 | EE 35 µg and CPA 2 mg | EE 35 µg and CPA 2 mg | EE 35 µg and CPA 2 mg |
| Day 30 | CPA 2 mg | CPA 2 mg | EE 15 µg and CPA 2 mg |

EXAMPLE 2

Stimulation of Plasma Concentrations Induced by Oral Contraceptive Pills Dosing Regimens To further explore the efficacy of an extended-cycle CPA/EE regimen for the treatment of PCOS, two additional regimens, consisting of 84 days on medication followed by 7 days off, were evaluated. Regimens 4 and 5 consist of the daily administration of 2 mg CPA and a varying, less frequent administration of 35 µg EE.

The objective of the current analysis was to compare and evaluate the following two candidate regimens (see also Table 2):

Regimen 4:
 Day 1-14: 35 µg EE daily+2 mg CPA daily
 Day 15-84: 35 µg EE every other day+2 mg CPA daily
Regimen 5:
 Day 1-84: 35 µg EE every other day+2 mg CPA daily

TABLE 2

Dosing regimens 4 and 5 summary

| | Sample Regimen 4 | Sample Regimen 5 |
|---|---|---|
| Day 1 | EE 35 µg and CPA 2 mg | EE 35 µg and CPA 2 mg |
| Day 2 | EE 35 µg and CPA 2 mg | CPA 2 mg |
| Day 3 | EE 35 µg and CPA 2 mg | EE 35 µg and CPA 2 mg |
| Day 4 | EE 35 µg and CPA 2 mg | CPA 2 mg |
| Day 5 | EE 35 µg and CPA 2 mg | EE 35 µg and CPA 2 mg |
| Day 6 | EE 35 µg and CPA 2 mg | CPA 2 mg |
| Day 7 | EE 35 µg and CPA 2 mg | EE 35 µg and CPA 2 mg |
| Day 8 | EE 35 µg and CPA 2 mg | CPA 2 mg |
| Day 9 | EE 35 µg and CPA 2 mg | EE 35 µg and CPA 2 mg |
| Day 10 | EE 35 µg and CPA 2 mg | CPA 2 mg |
| Day 11 | EE 35 µg and CPA 2 mg | EE 35 µg and CPA 2 mg |
| Day 12 | EE 35 µg and CPA 2 mg | CPA 2 mg |
| Day 13 | EE 35 µg and CPA 2 mg | EE 35 µg and CPA 2 mg |
| Day 14 | EE 35 µg and CPA 2 mg | CPA 2 mg |
| Day 15 | CPA 2 mg | EE 35 µg and CPA 2 mg |
| Day 16 | EE 35 µg and CPA 2 mg | CPA 2 mg |
| Day 17 | CPA 2 mg | EE 35 µg and CPA 2 mg |
| Day 18 | EE 35 µg and CPA 2 mg | CPA 2 mg |
| Day 19 | CPA 2 mg | EE 35 µg and CPA 2 mg |
| Day 20 | EE 35 µg and CPA 2 mg | CPA 2 mg |
| Day 21 | CPA 2 mg | EE 35 µg and CPA 2 mg |
| Day 21 | EE 35 µg and CPA 2 mg | CPA 2 mg |
| Day 23 | CPA 2 mg | EE 35 µg and CPA 2 mg |
| Day 24 | EE 35 µg and CPA 2 mg | CPA 2 mg |
| Day 25 | CPA 2 mg | EE 35 µg and CPA 2 mg |
| Day 26 | EE 35 µg and CPA 2 mg | CPA 2 mg |
| Day 27 | CPA 2 mg | EE 35 µg and CPA 2 mg |
| Day 28 | EE 35 µg and CPA 2 mg | CPA 2 mg |
| Day 29 | CPA 2 mg | EE 35 µg and CPA 2 mg |
| Day 30 | EE 35 µg and CPA 2 mg | CPA 2 mg |
| Day 31 | CPA 2 mg | EE 35 µg and CPA 2 mg |
| Day 32 | EE 35 µg and CPA 2 mg | CPA 2 mg |
| Day 33 | CPA 2 mg | EE 35 µg and CPA 2 mg |
| Day 34 | EE 35 µg and CPA 2 mg | CPA 2 mg |
| Day 35 | CPA 2 mg | EE 35 µg and CPA 2 mg |
| Day 36 | EE 35 µg and CPA 2 mg | CPA 2 mg |
| Day 37 | CPA 2 mg | EE 35 µg and CPA 2 mg |
| Day 38 | EE 35 µg and CPA 2 mg | CPA 2 mg |
| Day 39 | CPA 2 mg | EE 35 µg and CPA 2 mg |
| Day 40 | EE 35 µg and CPA 2 mg | CPA 2 mg |
| Day 41 | CPA 2 mg | EE 35 µg and CPA 2 mg |
| Day 42 | EE 35 µg and CPA 2 mg | CPA 2 mg |
| Day 43 | CPA 2 mg | EE 35 µg and CPA 2 mg |
| Day 44 | EE 35 µg and CPA 2 mg | CPA 2 mg |
| Day 45 | CPA 2 mg | EE 35 µg and CPA 2 mg |
| Day 46 | EE 35 µg and CPA 2 mg | CPA 2 mg |
| Day 47 | CPA 2 mg | EE 35 µg and CPA 2 mg |
| Day 48 | EE 35 µg and CPA 2 mg | CPA 2 mg |
| Day 49 | CPA 2 mg | EE 35 µg and CPA 2 mg |
| Day 50 | EE 35 µg and CPA 2 mg | CPA 2 mg |
| Day 51 | CPA 2 mg | EE 35 µg and CPA 2 mg |
| Day 52 | EE 35 µg and CPA 2 mg | CPA 2 mg |
| Day 53 | CPA 2 mg | EE 35 µg and CPA 2 mg |
| Day 54 | EE 35 µg and CPA 2 mg | CPA 2 mg |
| Day 55 | CPA 2 mg | EE 35 µg and CPA 2 mg |
| Day 56 | EE 35 µg and CPA 2 mg | CPA 2 mg |
| Day 57 | CPA 2 mg | EE 35 µg and CPA 2 mg |
| Day 58 | EE 35 µg and CPA 2 mg | CPA 2 mg |
| Day 59 | CPA 2 mg | EE 35 µg and CPA 2 mg |
| Day 60 | EE 35 µg and CPA 2 mg | CPA 2 mg |
| Day 61 | CPA 2 mg | EE 35 µg and CPA 2 mg |
| Day 62 | EE 35 µg and CPA 2 mg | CPA 2 mg |
| Day 63 | CPA 2 mg | EE 35 µg and CPA 2 mg |
| Day 64 | EE 35 µg and CPA 2 mg | CPA 2 mg |
| Day 65 | CPA 2 mg | EE 35 µg and CPA 2 mg |
| Day 66 | EE 35 µg and CPA 2 mg | CPA 2 mg |
| Day 67 | CPA 2 mg | EE 35 µg and CPA 2 mg |
| Day 68 | EE 35 µg and CPA 2 mg | CPA 2 mg |
| Day 69 | CPA 2 mg | EE 35 µg and CPA 2 mg |
| Day 70 | EE 35 µg and CPA 2 mg | CPA 2 mg |
| Day 71 | CPA 2 mg | EE 35 µg and CPA 2 mg |
| Day 72 | EE 35 µg and CPA 2 mg | CPA 2 mg |
| Day 73 | CPA 2 mg | EE 35 µg and CPA 2 mg |
| Day 74 | EE 35 µg and CPA 2 mg | CPA 2 mg |
| Day 75 | CPA 2 mg | EE 35 µg and CPA 2 mg |
| Day 76 | EE 35 µg and CPA 2 mg | CPA 2 mg |
| Day 77 | CPA 2 mg | EE 35 µg and CPA 2 mg |
| Day 78 | EE 35 µg and CPA 2 mg | CPA 2 mg |
| Day 79 | CPA 2 mg | EE 35 µg and CPA 2 mg |
| Day 80 | EE 35 µg and CPA 2 mg | CPA 2 mg |
| Day 81 | CPA 2 mg | EE 35 µg and CPA 2 mg |
| Day 82 | EE 35 µg and CPA 2 mg | CPA 2 mg |
| Day 83 | CPA 2 mg | EE 35 µg and CPA 2 mg |
| Day 84 | EE 35 µg and CPA 2 mg | CPA 2 mg |

The steady state exposure of CPA in the two candidate regimens is assumed to be similar to that observed following administration at steady state of Diane-35 (Kuhnz 1993). This assumption is supported by the fact that CPA steady state is achieved after approximately 16 days of daily administration and that the EE-induced changes in sex hormone-binding globulin (SHGB) levels do not impact the CPA pharmacokinetic (PK). Therefore, no notable accumulation beyond the CPA accumulation observed with Diane-35 by week 3 of the second or third cycle is expected following administration of 2 mg CPA QD for 84 days.

The simulations for PCOS patients were conducted using nonlinear mixed effects modelling (NONMEM®) program Version 7.4 (ICON Development Solutions, Ellicott City, Md.). All simulation input dataset preparation and output analyses were performed using R Version 4.0.3 (R Foundation for Statistical Computing, Vienna, Austria). Noncompartmental analysis of simulated concentration-time data was performed in R Version 4.0.3 using the PKNCA package version 0.9.4. Two publicly available population PK models of EE were selected to be evaluated for their predictive ability of the EE PK following Diane-35 administration, including a separate population PK model for EE, which was reported in U.S. FDA (2013) (referred to as the "Quartette PopPK model").

The popPK model was found to be the one that best predicts the steady-state EE PK from Diane-35 is the Quartette model. Therefore, this model was selected to simulate the EE candidate dosing regimens.

Due to the differences in dosing frequency between the simulated candidate dosing regimens (daily for 14 days, followed by administration every other day up to 84 days, or administration every other day for 84 days) compared to the daily administration of YAZ and Lo Loestrin, the most appropriate PK parameter for comparison is Cavg (see Table 3).

Figure 1B:
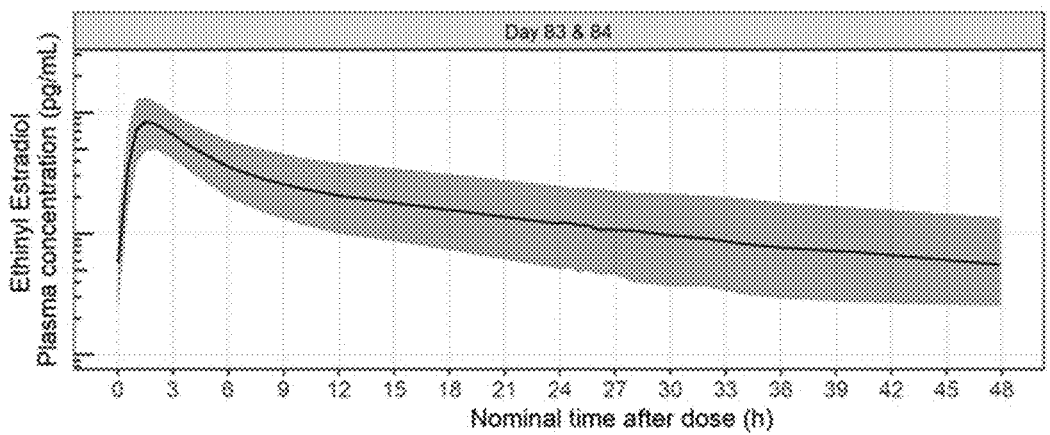

The results for Regimen 4 showed that the median Cavg on Day 14, following 14 days of daily administration is ~4-fold greater than the mean steady-state EE exposure for YAZ and ~1.4-fold greater than that for Lo Loestrin. In addition, the median Cavg on Day 83, following administration every other day on Days 15 to 84 is ~2.2-fold greater than the mean steady-state EE exposure for YAZ and ~1.3-fold lower than that for Lo Loestrin (see FIGS. 1A and 1B).

TABLE 3

Comparison of Model-Based Predicted EE PK Parameters for the two Candidate Regimens to the EE PK Parameters from YAZ and Lo Loestrin

| Regimen | Steady-State PK parameter (unit) | Day | Median [90% PI] | YAZ[3] (Day 21) Geo Mean (CVb) | Lo Loestrin[5] (Day 24) Mean (CV %) |
|---|---|---|---|---|---|
| 4 | Cmax (pg/mL) | 14 | 109 [71.5, 161] | 45.1 (35) | 71.3 (33) |
|   | AUC(0-τ) (pg*h/mL)[1] |  | 881 [561, 1460] | 220 (57) | 621.3 (41) |
|   | Cavg (pg/mL)[2] |  | 36.7 [23.4, 60.7] | 9.2 (n.a.)[4] | 25.9 (41) |
|   | Cmax (pg/mL) | 83 | 93.5 [59.4, 142] | 45.1 (35) | 71.3 (33) |
|   | AUC(0-τ) (pg*h/mL)[1] |  | 941 [619, 1510] | 220 (57) | 621.3 (41) |
|   | Cavg (pg/mL)[2] |  | 19.6 [12.9, 31.4] | 9.2 (n.a.)[4] | 25.9 (41) |
| 5 | Cmax (pg/mL) | 13 | 94.8 [61.1, 146] | 45.1 (35) | 71.3 (33) |
|   | AUC(0-τ) (pg*h/mL)[1] |  | 962 [634, 1500] | 220 (57) | 621.3 (41) |
|   | Cavg (pg/mL)[2] |  | 20.0 [13.2, 31.2] | 9.2 (n.a.)[4] | 25.9 (41) |
|   | Cmax (pg/mL) | 83 | 93.8 [60.6, 149] | 45.1 (35) | 71.3 (33) |
|   | AUC(0-τ) (pg*h/mL)[1] |  | 968 [640, 1510] | 220 (57) | 621.3 (41) |
|   | Cavg (pg/mL)[2] |  | 20.2 [13.3, 31.5] | 9.2 (n.a.)[4] | 25.9 (41) |

Regimen 1: 35 μg QD days 1 to 14 and 35 μg QOD days 15-84;

Regimen 2: 35 μg QOD days 1-84

PI = prediction interval;

Geo mean = geometric mean;

CVb = geometric coefficient of variation

[1]Steady state AUC calculated over the dosing interval [τ], where τ = 24 h for regimen 1, day 14 or τ = 48 h for regimen 1, day 83 or regimen 2, days 13 and 84.

[2]Cavg calculated as steady state AUC/τ

[3]Drospirenone 3 mg/EE 0.02 mg

[4]Calculated as AUC(0-24)/24 for YAZ

[5]Norethindrone 1 mg/EE 0.01 mg; data shown as arithmetic mean (coefficient of variation)

Figure 2A:
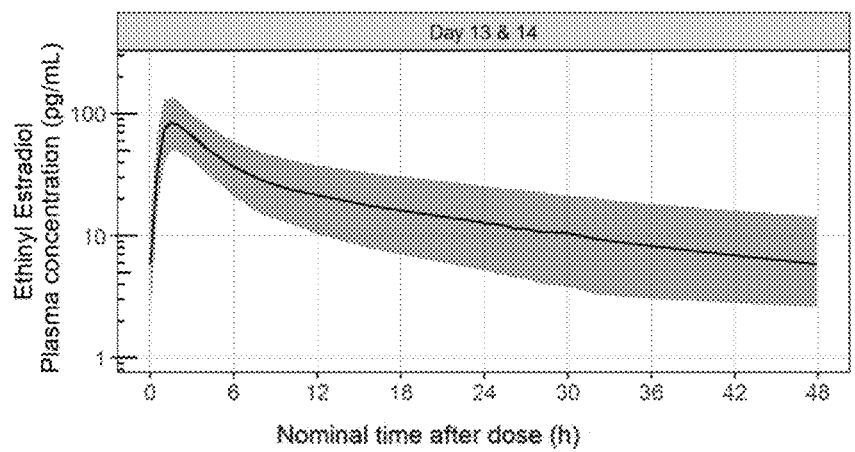
FIGS. 2A-2B illustrate simulated EE plasma concentrations of a dosing regimen including 35 μg EE every other day from day 1 to 84.
Figure 2B:
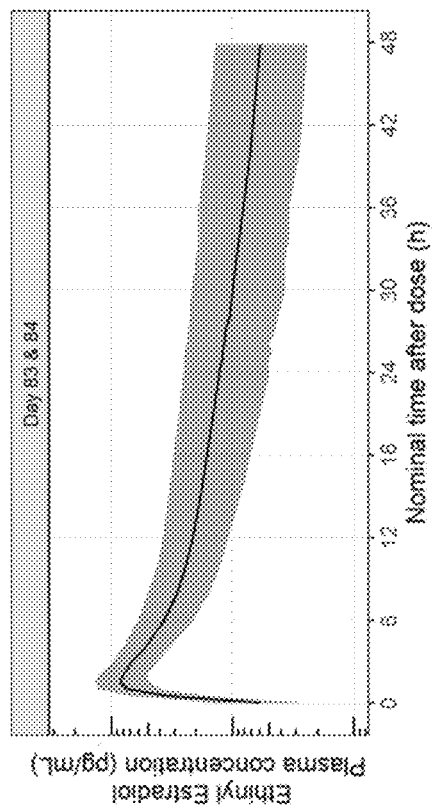

For Regimen 5, the results showed that the median Cavg on Days 13 and 83 following administration every other day is ~2.2-fold greater than the mean steady-state EE exposure for YAZ and ~1.3-fold lower than that for Lo Loestrin (see FIGS. 2A and 2B). The Quartette popPK model with bioavailability 100% (F=1) showed the lowest bias between the predicted and observed steady-state exposure for Diane-35 and was selected for simulations of dosing regimen Both regimens resulted in similar steady-state exposures (Cavg) after multiple doses every other day that were ~2.2-fold greater than those observed with YAZ and ~1.3-fold lower compared to the steady-state exposure from Lo Loestrin.

Based on the similarity in exposure at steady state for most of the duration of the dosing regimen, no notable difference in efficacy is expected between the two candidate regimens.

EXAMPLE 3

Evaluation of the Efficacy of Combination Oral Contraceptive Pills Dosing Regimens To evaluate the efficacy of the three dosing regimens described in Example 1, a Phase 1 study will be implemented, to assess the patient serum hormone levels provided by the dosing regimen as compared with a reference OCP.

The effects on hyperandrogenic conditions and/or hyperandrogenic activities, such as symptoms of PCOS, acne, severe acne, seborrhea, and mild hirsutism will also be assessed. The incidence of vascular thromboembolism (VTE) will also be evaluated either during the study or post-marketing approval.

EMBODIMENTS OF THE INVENTION

In addition to the aspects and embodiments described and provided elsewhere in this disclosure, the following non-limiting list of particular embodiments are specifically contemplated.
1. An oral drug preparation comprising:
(a) a first composition comprising about 5 to 50 µg ethinylestradiol (EE) and about 1 to 10 mg progestin; and
(b) a second composition comprising about 1 to 10 mg progestin, wherein, beginning on day 15 of a dosing schedule, the second composition is administered on day 15 and then every other day.
2. The preparation of embodiment 1, wherein the first composition is administered to the subject: daily beginning on day 1 of the dosing schedule and for 14 consecutive days, inclusive, and every other day beginning on day 16 of the dosing schedule.
3. The preparation of embodiment 1, wherein the progestin is cyproterone acetate (CPA).
4. The preparation of embodiment 3, wherein the first composition comprises about 35 µg EE and about 2 mg CPA.
5. The preparation of embodiment 1, wherein the second composition comprises about 2 mg CPA.
6. The preparation of embodiment 1, wherein the dosing schedule is about 84 days.
7. The preparation of embodiment 1, further comprising a third composition comprising no active ingredient.
8. The preparation of embodiment 7, wherein beginning the day following the last day of the dosing schedule, the third composition with no active ingredient is administered daily for 4 to 7 consecutive days, inclusive.

9. An oral drug preparation comprising:
(a) a first composition comprising about 5 to 50 µg ethinylestradiol (EE) and about 1 to 10 mg progestin; and
(b) a second composition comprising about 1 to 10 mg progestin, wherein beginning on day 8 of a dosing schedule, the second composition is administered on day 8 and then every other day.
10. The preparation of embodiment 9, wherein the progestin is cyproterone acetate (CPA).
11. The preparation of embodiment 10, wherein the first composition comprises about 35 µg EE and about 2 mg CPA.
12. The preparation of embodiment 9, wherein the second composition comprises about 2 mg CPA.
13. The preparation of embodiment 9, wherein beginning on day 1 of the dosing schedule, the first composition is administered on day 1 and then every other day.
14. The preparation of embodiment 13, wherein beginning on day 2 of the dosing schedule, the second composition is further administered on day 2 and then every other day.
15. The preparation of embodiment 9, wherein the first composition is administered to the subject: daily beginning on day 1 of the dosing schedule and for 7 consecutive days, inclusive, and every other day beginning on day 9 of the dosing schedule.
16. The preparation of embodiment 9, wherein the dosing schedule comprises 21, 30, 49 or 84 days.
17. The preparation of embodiment 9, further comprising a third composition comprising no active ingredient.
18. The preparation of embodiment 17, wherein beginning the day following the last day of the dosing schedule, the third composition with no active ingredient is administered daily for 4 to 7 consecutive days, inclusive.
19. An oral drug preparation comprising:
a) a first composition comprising about 5 to 50 µg ethinylestradiol (EE) and about 1 to 10 mg progestin; and
b) a second composition comprising about 5 to 50 µg ethinylestradiol (EE) and about 1 to 10 mg progestin;
wherein the second composition comprises a lower amount of EE as compared to the first composition, and wherein the first and second compositions are administered to a subject on alternating days on a 30-day dosing schedule.
20. The preparation of embodiment 19, wherein the first composition is administered on day 1 of the 30-day dosing schedule.
21. The preparation of embodiment 19, wherein the progestin is cyproterone acetate (CPA).
22. The preparation of embodiment 21, wherein the first composition comprises about 35 µg EE and about 2 mg CPA.
23. The preparation of embodiment 19, wherein the second composition comprises about 15 EE and about 2 mg CPA.
24. A method of treating one or more symptoms of hyperandrogenic conditions or hyperandrogenic activities in a subject comprising administering to the subject the preparations of any one of embodiment 1, 9 or 19, thereby treating one or more symptoms of hyperandrogenic conditions or hyperandrogenic activities in the subject.
25. The method of embodiment 24, wherein the preparation comprises:
(a) a first composition comprising about 35 µg EE and about 2 mg CPA; and
(b) a second composition comprising about 2 mg CPA, wherein beginning on day 15 of a dosing schedule, the second composition is administered on day 15 and then every other day.

26. The method of embodiment 25, the first composition is administered to the subject: daily beginning on day 1 of the dosing schedule and for 14 consecutive days, inclusive, and every other day beginning on day 16 of the dosing schedule.
27. The method of embodiment 25, further comprising a third composition comprising no active ingredient.
28. The method of embodiment 27, wherein beginning the day following the last day of the dosing schedule, the third composition with no active ingredient is administered daily for 4 to 7 consecutive days, inclusive.
29. The method of embodiment 25, wherein the preparation is administered over a 84-day administration period.
30. The method of embodiment 24, wherein the one or more symptoms of hyperandrogenic conditions or hyperandrogenic activities is selected from the group consisting of polycystic ovary syndrome (PCOS), acne, severe acne, seborrhea, mild hirsutism and excessive hair growth.
31. A method of providing contraception to a female subject comprising administering to the subject the preparation of any one of embodiment 1, 9 or 19, thereby providing contraception to the female subject.
32. The method of embodiment 31, wherein the preparation comprises:
(a) a first composition comprising about 35 µg EE and about 2 mg CPA; and
(b) a second composition comprising about 2 mg CPA, wherein beginning on day 15 of a dosing schedule, the second composition is administered on day 15 and then every other day.
33. The method of embodiment 32, wherein the first composition is administered to the subject: daily beginning on day 1 of the dosing schedule and for 14 consecutive days, inclusive, and every other day beginning on day 16 of the dosing schedule.
34. A method of reducing a risk of vascular thromboembolism (VTE) in a subject comprising administering to the subject the preparation of any one of embodiment 1, 9 or 19, thereby reducing the risk of VTE in the subject.
35. The method of embodiment 34, wherein the preparation comprises:
(a) a first composition comprising about 35 µg EE and about 2 mg CPA; and
(b) a second composition comprising about 2 mg CPA, wherein beginning on day 15 of a dosing schedule, the second composition is administered on day 15 and then every other day.
36. The method of embodiment 35, wherein the first composition is administered to the subject: daily beginning on day 1 of the dosing schedule and for 14 consecutive days, inclusive, and every other day beginning on day 16 of the dosing schedule.
37. An oral drug preparation comprising:
(a) a first composition comprising about 5 to 50 µg ethinylestradiol (EE) and about 1 to 10 mg CPA;
(b) a second composition comprising a high amount of EE and about 1 to 10 mg CPA;
(c) a third composition comprising a low amount of EE and about 1 to 10 mg CPA; and
(d) a fourth composition comprising no EE and no CPA, wherein:
(i) beginning on day 1 of a dosing schedule, the first composition is administered daily for 0-14 days,
(ii) beginning after (i) and for about 21-84 days, the second and third compositions are administered alternatively every other day, and
(iii) beginning after (ii) and for about 0-7 days, the fourth composition is administered daily.
38. A method of providing contraception to a female subject comprising controlling an hormonal profile of the subject using a triphasic oral drug regimen, wherein controlling the hormonal profile of the subject comprises:
(a) administering daily to the subject a composition comprising 5-50 µg EE and 1-10 mg CPA for 0 to 14 days;
(b) administering to the subject on an alternate schedule a first composition including 5-50 µg EE and 1-10 mg CPA and a second composition including 0-50 µg EE and 1-10 mg CPA, for 21 to 84 days; and
(c) administering daily to the subject a composition comprising no EE and no CPA for 0 to 7 days,
thereby providing contraception to the female subject.
39. A pharmaceutical package comprising the oral preparation of any of embodiment 1, 9, 19 or 37.
40. The pharmaceutical package of embodiment 39, further comprising instructions for administration of or ingestion of the oral preparation.

Although the invention has been described with reference to the above examples, it will be understood that modifications and variations are encompassed within the spirit and scope of the invention. Accordingly, the invention is limited only by the following claims.

What is claimed is:
1. An oral drug preparation comprising:
(a) a first composition comprising about 5 to 50 µg ethinylestradiol (EE) and about 1 to 10 mg cyproterone acetate (CPA); and
(b) a second composition consisting essentially of about 1 to 10 mg CPA, wherein, beginning on day 15 of a dosing schedule, the second composition is administered on day 15 and then every other day.
2. The preparation of claim 1, wherein the first composition is administered to the subject: daily beginning on day 1 of the dosing schedule and for 14 consecutive days, inclusive, and every other day beginning on day 16 of the dosing schedule.
3. The preparation of claim 1, wherein the first composition comprises about 35 µg EE and about 2 mg CPA.
4. The preparation of claim 1, wherein the CPA in the second composition is about 2 mg CPA.
5. The preparation of claim 1, wherein the dosing schedule is about 84 days.
6. The preparation of claim 1, further comprising a third composition comprising no active ingredient.
7. The preparation of claim 6, wherein beginning the day following the last day of the dosing schedule, the third composition with no active ingredient is administered daily for 4 to 7 consecutive days, inclusive.
8. An oral drug preparation comprising:
(a) a first composition comprising about 5 to 50 µg ethinylestradiol (EE) and about 1 to 10 mg cyproterone acetate (CPA); and
(b) a second composition consisting essentially of about 1 to 10 mg CPA, wherein beginning on day 8 of a dosing schedule, the second composition is administered on day 8 and then every other day.
9. The preparation of claim 8, wherein the first composition comprises about 35 µg EE and about 2 mg CPA.
10. The preparation of claim 8, wherein the CPA in the second composition is about 2 mg CPA.
11. The preparation of claim 8, wherein beginning on day 1 of the dosing schedule, the first composition is administered on day 1 and then every other day.

12. The preparation of claim 11, wherein beginning on day 2 of the dosing schedule, the second composition is further administered on day 2 and then every other day.

13. The preparation of claim 8, wherein the first composition is administered to the subject: daily beginning on day 1 of the dosing schedule and for 7 consecutive days, inclusive, and every other day beginning on day 9 of the dosing schedule.

14. The preparation of claim 8, wherein the dosing schedule comprises 21, 28, 49 or 84 days.

15. The preparation of claim 8, further comprising a third composition comprising no active ingredient.

16. The preparation of claim 15, wherein beginning the day following the last day of the dosing schedule, the third composition with no active ingredient is administered daily for 4 to 7 consecutive days, inclusive.

17. An oral drug preparation comprising:
 a) a first composition comprising about 5 to 50 µg ethinylestradiol (EE) and about 1 to 10 mg cyproterone acetate (CPA); and
 b) a second composition comprising about 5 to 50 µg ethinylestradiol (EE) and about 1 to 10 mg cyproterone acetate (CPA);
 wherein the second composition comprises a lower amount of EE as compared to the first composition, and
 wherein the first and second compositions are administered to a subject on alternating days on a 30-day dosing schedule.

18. The preparation of claim 17, wherein the first composition is administered on day 1 of the 30-day dosing schedule.

19. The preparation of claim 17, wherein the first composition comprises about 35 µg EE and about 2 mg CPA and the second composition comprises about 15 µg EE and about 2 mg CPA.

20. A method of treating one or more symptoms of hyperandrogenic conditions or hyperandrogenic activities in a subject comprising administering to the subject the preparation of claim 1, thereby treating one or more symptoms of hyperandrogenic conditions or hyperandrogenic activities in the subject.

21. The method of claim 20, wherein the first composition comprises about 35 µg EE and about 2 mg CPA; and the second composition comprises about 2 mg CPA.

22. The method of claim 20, beginning on day 1 of the dosing schedule and for 14 consecutive days, inclusive, the first composition is administered daily to the subject.

23. The method of claim 20, further comprising, beginning the day following the last day of the dosing schedule, administering to the subject a third composition comprising no active ingredient.

24. The method of claim 20, wherein the one or more symptoms of hyperandrogenic conditions or hyperandrogenic activities is selected from the group consisting of polycystic ovary syndrome (PCOS), acne, severe acne, seborrhea, mild hirsutism and excessive hair growth.

25. The method of claim 20, wherein administering the preparation further provides contraception to the subject.

26. A method of treating one or more symptoms of hyperandrogenic conditions or hyperandrogenic activities in a subject comprising administering to the subject the preparation of claim 8, thereby treating one or more symptoms of hyperandrogenic conditions or hyperandrogenic activities in the subject.

27. The method of claim 26, wherein beginning on day 1 of the dosing schedule, the first composition is administered on day 1 and then every other day, and beginning on day 2 of the dosing schedule, the second composition is further administered on day 2 and then every other day.

28. The method of claim 26, wherein beginning on day 1 of the dosing schedule and for 7 consecutive days, inclusive, the first composition is administered daily to a subject.

29. A method of treating one or more symptoms of hyperandrogenic conditions or hyperandrogenic activities in a subject comprising administering to the subject the preparation of claim 17, thereby treating one or more symptoms of hyperandrogenic conditions or hyperandrogenic activities in the subject.

30. A pharmaceutical package comprising the oral preparation of claim 1, optionally including instructions for use.

* * * * *